(12) United States Patent
Konishi et al.

(10) Patent No.: US 8,110,385 B2
(45) Date of Patent: Feb. 7, 2012

(54) LINEAR AND MEMBRANE-LIKE BIODEVICES AND BIOREACTORS

(75) Inventors: Satoshi Konishi, Kanagawa (JP); Tetsuya Miwa, Kanagawa (JP)

(73) Assignee: Japan Agency for Marine-Earth Science and Technology, Kanagawa (JP)

(*) Notice: Subject to any disclaimer, the term of this patent is extended or adjusted under 35 U.S.C. 154(b) by 2039 days.

(21) Appl. No.: 11/169,910

(22) Filed: Jun. 30, 2005

(65) Prior Publication Data

US 2006/0240547 A1    Oct. 26, 2006

(30) Foreign Application Priority Data

Apr. 25, 2005 (JP) .................... 2005-126378

(51) Int. Cl.
*C12N 11/08* (2006.01)
*C12N 11/04* (2006.01)
*C12N 5/00* (2006.01)

(52) U.S. Cl. .............. 435/180; 435/297.2; 435/299.1; 435/182; 435/398; 435/401; 435/399

(58) Field of Classification Search .............. 435/297.2, 435/180, 182, 398, 401, 299.1, 399
See application file for complete search history.

(56) References Cited

U.S. PATENT DOCUMENTS

| | | | | |
|---|---|---|---|---|
| 5,518,915 A | * | 5/1996 | Naughton et al. | 424/422 |
| 7,001,328 B1 | * | 2/2006 | Barofsky et al. | 600/36 |
| 2005/0147642 A1 | * | 7/2005 | Laredo et al. | 424/423 |

FOREIGN PATENT DOCUMENTS

| | | |
|---|---|---|
| JP | 7-298876 A | 11/1995 |
| JP | 8-33473 A | 2/1996 |
| JP | 8-33474 A | 2/1996 |
| JP | 8-33475 A | 2/1996 |

OTHER PUBLICATIONS

Felemovicius et al., Prevention of Adhesions to Polypropylene Mesh, American College of Surgeons, Apr. 2004, pp. 543-548, vol. 198—No. 4.
Pei et al., Bioreactors Mediate the Effectiveness of Tissue Engineering Scaffolds, The FASEB Journal, Oct. 2002, pp. 1691-1694, vol. 16.
Kral et al., Development of a Human Adipocyte Synthetic Polymer Scaffold, Department of Surgery at SUNY Downstate Medical Center and Wyeth-Ayerst Research, Nov. 1999, pp. 1732-1738, vol. 104—No. 6.
Mayer et al, Matrices for Tissue Engineering-Scaffold Structure for a Bioartificial Liver Support System, Journal of Controlled Release 64, 2000, pp. 81-90.
Vehof et al., Bone Formation in CaP-Coated and Noncoated Titanium Fiber Mesh, 2003, pp. 417-426.

\* cited by examiner

*Primary Examiner* — Nathan Bowers
(74) *Attorney, Agent, or Firm* — Sughrue Mion, PLLC

(57) ABSTRACT

A linear biodevice is provided with fibers that have a curved portion in its cross section approximately perpendicular to the longitudinal direction and approximately spherical adhesive cells that adhere to the periphery of the fiber. A membrane-like biodevice is provided with a sheet that has an opening and approximately spherical adhesive cells that adhere to the opening. A curved portion is present in the cross section on an inner edge of the opening. A bioreactor is provided with a membrane-like biodevice in which spherical adhesive cells grow densely so as to close the openings of the sheet.

6 Claims, 1 Drawing Sheet

LINEAR AND MEMBRANE-LIKE BIODEVICES AND BIOREACTORS

BACKGROUND OF THE INVENTION

1) Field of the Invention

The present invention relates to a linear biodevice, a membrane-like biodevice and a bioreactor using them, and more specifically to a linear or membrane-like biodevices and a bioreactor in which adhesive cells are anchored at high density.

The biodevices and the bioreactor of the present invention are useful for production, conversion, or separation of a useful substance by taking advantage of adhesive cells.

2) Description of the Related Art

Conventionally, as to a method of making cells in a membrane-like form, there is a method in which cells anchored to a flat bottom surface of a container that has been treated with a temperature sensitive polymer are detached by taking advantage of extension of the temperature sensitive polymer, and the method is used for regeneration of cornea and the like.

Further, various properties and forms of materials have been studied as a carrier to which adhesive cells are anchored. In a bioreactor, adhesive cells are anchored to a flat surface arranged in a flow path or a fiber aggregate.

In recent years, a permeable cell culture carrier, and a culture method and a culture device that use this carrier have been proposed (for example, Japanese Patent Application Laid-Open Publication No. 1995-298876), and it has been disclosed that when any one of a plurality of natural or synthetic threads and textile or both are used as a carrier, permeability can be secured, animal cells proliferate three-dimensionally, and tissues can be self-formed with a high survival rate.

Further, with respect to a culture substrate for adhesive animal cells, it has been disclosed (for example, Japanese Patent Application Laid-Open Publication No. 1996-33743, Japanese Patent Application Laid-Open Publication No. 1996-33474, and Japanese Patent Application Laid-Open Publication No. 1996-33475) that when the culture substrate that has a basic functional group, an acidic functional group, or a neutral functional group on a fiber aggregate constituted of fibers of 20 to 60-micrometer fiber diameters and formed in a manner that the fibers are intertwined with one another with fiber surface area of 10 to 30 $m^2/m^3$ and porosity of 90% is used, the cells adhere to the fiber surface, proliferate, and extend, and further exhibit multilayered growth, and therefore, it is possible to immobilize the cells at high density and form a porous structure.

However, such a conventional technology has the following problems.

That is, since there is no supporter in a cell sheet prepared by detaching cells that have been immobilized to a flat bottom surface of a culture container, a strength of the sheet alone is not sufficient, which gives rise to a problem that handling becomes complex.

Further, when cells are anchored to a flat bottom surface of a culture container, the cells extend to adhere to it. Therefore, not only do the cells occupy an area that is several times of the cell diameter in suspension but also proliferation of the cells stops in a confluent state, which gives rise to a problem that the cells cannot be immobilized at high density.

When a porous material is used as a carrier, it is difficult for cells to be formed in a membrane-like shape, and it is impossible for the cells to be immobilized at high density. Further, it is also impossible to swiftly supply oxygen and nutrients essential for animal cells to the inside of the carrier, which gives rise to another problem that only the vicinity of the surface of the carrier functions.

On the other hand, when a fiber aggregate is used as a carrier, it is so porous that convection takes place owing to good permeability, which does not allow cells to be immobilized at high density and the carrier to which the cells are anchored to play a role of a partition, and therefore, it is impossible to allow the cells to make contact with two kinds of fluids without being mixed with each other.

SUMMARY OF THE INVENTION

The present invention has been carried out by taking it into consideration that such a conventional technology has the problems, and objects of the present invention are to provide a linear biodevice, a membrane-like biodevice and a bioreactor to which adhesive cells can be efficiently immobilized at high density and which are excellent in handling and applicability.

As the result of assiduous research to achieve the above objects, the present inventors completed the present invention by finding that when fibers having a predetermined form of cross section, a sheet having an opening, or the like is used as a carrier, cells that adhere to the periphery of the fiber and to the inner edge of the opening proliferate while retaining their spherical shape without extending, which leads to a high rate of cell adherence at high density, thereby achieving the above objects.

That is, the linear biodevice of the present invention is characterized by comprising a fiber having a curved portion in a cross section approximately perpendicular to a longitudinal direction and approximately spherical adhesive cells adhering to a periphery of the fiber.

Further, a preferred embodiment of the linear biodevice of the present invention is characterized in that the spherical adhesive cells adhere to the curved portion in the cross section on the periphery of the fiber.

Furthermore, another preferred embodiment of the linear biodevice of the present invention is characterized in that a diameter of each of the spherical adhesive cells are from 5 to 50 micrometers and the fiber diameter of the fiber is equal to or smaller than 80 micrometers.

On the other hand, the membrane-like biodevice of the present invention comprises a sheet having an opening and approximately spherical adhesive cells adhering to the opening, and is characterized in that a curved portion is present in the cross section on the inner edge of the opening.

A preferred embodiment of the membrane-like biodevice of the present invention is characterized in that the sheet have a plurality of openings approximately in the same shapes, and the openings are arranged at a predetermined pitch.

Further, the preferred embodiment of the membrane-like biodevice of the present invention is characterized in that a maximum length of the opening is from a particle diameter of the spherical adhesive cell immediately after cell division to ten times the particle diameter after cell growth.

Furthermore, another preferred embodiment of the membrane-like biodevice of the present invention is characterized in that a maximum length of the opening is from 10 to 80 micrometers.

Still further, still another preferred embodiment of the membrane-like biodevice of the present invention is characterized in that the sheet is made of mesh-like fibers that have a curved portion in its cross section approximately perpendicular to the longitudinal direction.

Still further, still another preferred embodiment of the membrane-like biodevice of the present invention is characterized in that the spherical adhesive cells grow densely so as to close the openings of the sheet.

Still further, a bioreactor of the present invention is characterized by provision of a membrane-like biodevice as described above.

DETAILED DESCRIPTION

Figure 1:
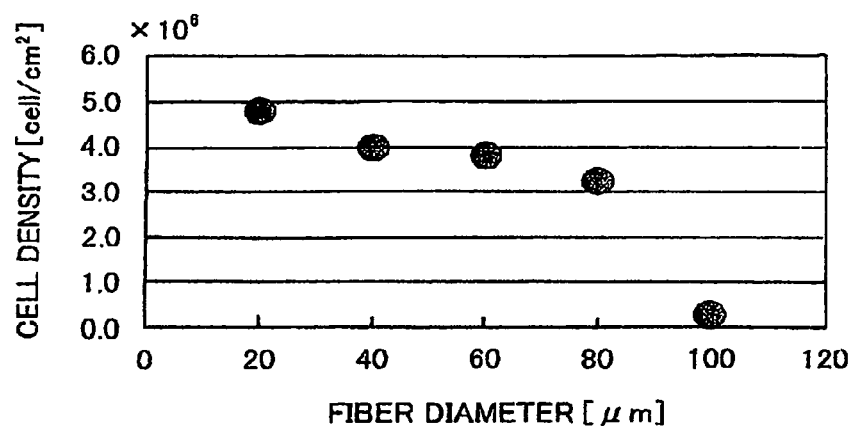
FIG. 1 is a graph that represents a relation between cell density and fiber diameter.

Hereinafter, a linear biodevice of the present invention will be explained in detail. In the present specification and claims, "%" represents mass percentage as long as it is not specified. In addition, "approximately" means a range including a measurement error and the like, and an action effect of the present invention is offered within the range.

As described above, the linear biodevice of the present invention has fibers that have a curved portion in its cross section approximately perpendicular to the longitudinal direction and approximately spherical adhesive cells, and the spherical adhesive cells adhere to the periphery of the fibers serving as a carrier, respectively.

Further, the entire shape of the linear biodevice of the present invention may be linear or curved, and further may be serpiginous like S letter.

Here, material of the fiber that functions as a carrier is not particularly limited, and various organic fibers or inorganic fibers can be used. The organic fibers can include various natural and synthetic fibers, for example, natural fibers such as silk and cotton, and synthetic fibers such as nylon (trademark), acryl, and polyester. On the other hand, the inorganic fibers can include various metal fibers, glass fibers, and ceramic fibers.

As to the organic fibers, a synthetic fiber whose surface is flat and the synthetic fiber whose surface is modified can be preferably used. Further, when an application to a field of regenerative medicine is taken into consideration, the use of biodegradable fibers is also effective.

The fiber used in the present invention has a curved portion in its cross section approximately perpendicular to the longitudinal direction, and the fiber can typically include fibers whose cross sections are circular and elliptic.

Note that a fiber is sufficient for use in the present invention when it has a curved portion present in at least part of cross section of the fiber, and therefore even a fiber whose cross section is subjected to round (R) processing or chamfering at its triangle or polygon corners can also be used.

According to the observation by the present inventors, the adhesive cells adhere to the fiber periphery constituting the curved portion preferentially or selectively to proliferate while retaining their spherical shape. However, the adhesive cells that have adhered to portions whose cross sections are straight cannot retain their spherical shape and they often tend to extend.

As described in the foregoing, fibers that have such shapes in their cross sections suffice for the fibers in the present invention, and therefore, whether the fiber is monofilament or multifilament is withdrawn from consideration as long as the fiber has such a cross section. Further, not only fibers in a narrow sense but also twisted threads and the like can be used.

The fiber diameter of the fiber can be appropriately changed in accordance with the kind and size (particle diameter) of an adhesive cell to be cultured, and typically, a fiber that has a fiber diameter equal to or smaller than 80 micrometers is preferably used for adhesive cells with a particle diameter of 5 to 50 micrometers, and preferably of 10 to 30 micrometers. The adhesive cells have a high probability of proliferation while retaining their spherical shape without extending when they adhere to fibers whose fiber diameter is equal to or smaller than 80 micrometers, and are easy to be immobilized at high density.

On the other hand, when the fiber diameter exceeds 80 micrometers, the adhesive cells extend after adhesion, which makes it difficult for the cells to be immobilized at high density.

Cells targeted for being used in the present invention are adhesive cells. When the fibers predetermined in the present invention described above are used for cultivation, the adhesive cells grow while retaining their spherical shape in their initial state. Therefore, the linear biodevice of the present invention is realized by anchoring spherical adhesive cells to the periphery of the predetermined fibers.

Although such adhesive cells are not particularly limited, the cells can especially include adhesive animal cells, for example, animal fibroblast and nerve cell.

When the adhesive cells are suspended in a culture medium at a density of approximately $10^5$ to $10^6$ cells/mL, allowed to come in contact with the fibers serving as a carrier and to proliferate under shake culture conditions, the linear biodevice of the present invention can be obtained with ease.

The culture medium used at this time may be a standard culture medium used when cells are cultured in a culture bottle.

Next, a membrane-like biodevice of the present invention will be explained.

As described above, the membrane-like biodevice of the present invention is provided with a sheet having an opening and spherical adhesive cells. The opening has a curved portion in the cross section of its inner edge, and the spherical adhesive cells adhere and are anchored to the inside of the opening.

The sheet for use here is sufficient as long as it is in a sheet form and has openings explained below. The sheet may be not only a sheet so-called sheet with open pore integrally formed but also fabric, textile, mesh, and the like made of the fibers described above.

However, in the present invention, a sheet in which a plurality of openings that are approximately in the same shape and are perforated and arranged with a predetermined pitch is useful. Owing to this, immobilized adhesive cells are orderly (at regular intervals) arranged, and the immobilized cells are uniformly distributed and arranged, thereby realizing a membrane-like biodevice excellent in homogeneity as a whole.

The material of the sheet may be organic materials or inorganic materials such as resin, ceramics, metal, and glass and is not particularly limited.

The shape of plane of the opening is not particularly limited, and the shape may be star and the like besides circle, ellipse, triangle, or tetragon or higher polygons.

However, with respect to the cross section of the inner edge of the opening, a curved portion is required to be at least partially present in the cross section. There is a high possibility that the adhesive cells preferentially and selectively adhere to the curved portions to grow and proliferate while retaining their spherical shape.

The curved portion is usually formed so as to protrude in the center direction of the opening.

The size of the opening can be appropriately selected in accordance with the size of adhesive cells to be immobilized, and typically the maximum length of the opening is preferred to be from a particle diameter of the adhesive cells in a spherical shape immediately after cell division to approximately ten times the particle diameter after cell growth.

"The maximum length of the opening" here means the longest length in the lines that can be drawn within the outline of the opening.

When the maximum length of the opening is shorter than the particle diameter immediately after cell division of the adhesive cell, the adhesive cells are not immobilized inside the opening, and when it exceeds ten times the particle diameter after cell growth, it becomes difficult for the cells to adhere so as to close the opening because fibers making up the opening are separated from one another too much, and therefore, a cavity is produced at the center of the opening, which often leads to a low density.

Generally, the size of the adhesive cells having a particle diameter of 5 to 50 micrometers varies in the process where cell division and growth are repeated, and the particle diameter after cell growth is increased up to approximately 1.5-fold compared to the particle diameter immediately after cell division.

In the preferred embodiment of the membrane-like biodevice of the present invention, the sheet described above is made in a mesh-like form of the above fibers, particularly of an organic fiber having a fiber diameter that is equal to or smaller than 80 micrometers and has approximately square openings each of which is 10 to 80 micrometers in size.

When the opening size of the opening is smaller than 10 micrometers, the adhesive cells do not infiltrate into the opening and extend so as to cover the surface of the mesh to adhere, and therefore, it becomes difficult for the cells to be immobilized at high density.

On the other hand, even though the adhesive cells are allowed to adhere when the opening size of the opening exceeds 80 micrometers, it becomes difficult for the cells to be immobilized so as to close the opening because the fibers making up the opening are separated from one another too much. As the result, the probability that pores remain open becomes high, and it becomes difficult to realize a further high density. Moreover, a role to serve as a partition described later cannot be played in some cases.

Compared to this, according to the preferred embodiment of the membrane-like biodevice of the present invention, when the adhesive cells are allowed to adhere to a mesh that is made of fibers having a fiber diameter that is equal to or smaller than 80 micrometers as well as made with an opening size of 10 to 80 micrometers, the cells proliferate so as to cover the opening to form a membrane-like device in which the mesh serves as a supporter (carrier).

Further, the number of the cells in multilayer in the thickness direction of the membrane-like biodevice is only ca. ten. Therefore, it is easy to supply oxygen and nutrients swiftly to these cells that have adhered to one another, which makes it possible to enhance a culture efficiency.

In accordance with closing of the opening, the adhesive cells each of which is originally in an approximately spherical shape sometimes become cubic or rectangular parallelepiped in a membrane region where the cells adhere to one another to be immobilized.

Further, in the membrane-like biodevice of the present invention, when the adhesive cells in a spherical shape are immobilized so as to close the openings of the sheet, convection that passes through the immobilized cells does not take place. Therefore, even if two different fluids are supplied to the surface side (one face side) and the back surface side (the other face side) of the membrane-like device, respectively, it is possible to suppress or avoid mixing of both fluids and supply two kinds of culture media and the like to the immobilized cells at the same time because the immobilized cells or the membrane-like biodevice itself can function as a partition.

A method for forming the membrane-like biodevice of the present invention is the same as that for forming the linear biodevice described above except for using a sheet having the openings described above as a carrier.

Next, a bioreactor of the present invention will be explained.

As described above, the bioreactor of the present invention from among the membrane-like biodevices of the present invention described above is provided with a membrane-like device in which its openings are closed by immobilized cells.

In such a membrane-like device, generation of fluid current that passes through the surface side and the back surface side thereof is suppressed or avoided. Therefore, when two spaces (two systems) that are partitioned by the membrane-like biodevice in a bioreactor are formed, components of culture medium and metabolic products from cells can move only by diffusion. Thus, with the use of the membrane-like device, it becomes possible to allow cells to come in contact with two different fluids without being mixed with each other.

From the foregoing, the use of the bioreactor of the present invention makes it possible to, for example, supply culture media of different components to cells independently and control supply rate and concentration of each culture medium independently. Moreover, it becomes possible to recover useful materials continuously by allowing a culture medium and a recovery fluid to keep in contact with the surface and the back surface of the membrane-like device, respectively.

Further, the membrane-like device is allowed to function as a selective permeable membrane by immobilizing appropriate cells, and therefore application to tests by taking advantage of selective permeability of cells and so forth becomes possible.

EXAMPLE

Hereinafter, a few examples of the present invention will be explained in more detail. However, the present invention is not limited by these examples.

Example 1

Nylon (trademark) fibers having fiber diameters of 20, 40, 60, 80, and 100 micrometers, respectively, and a 5 millimeter length were immersed in a culture medium [DMEM (Dulbecco's modified Eagle's medium)–high glucose (product of SIGMA, D6429), 10% FBS (fetal bovine serum)] containing mouse fibroblast 3T3L1 at $10^6$ cells/mL and subjected to shake culture. The culture medium was exchanged with a fresh culture medium every three days.

The fibers were taken out after ten days, and the number of the cells was counted after detaching the cells having adhered to the fibers from the fibers by trypsin, followed by calculating the density of the cells adhering to the fibers with reference to fiber surface area. The obtained results are shown in FIG. 1.

When the fiber diameter was equal to or smaller than 80 micrometers, the cell density was higher than $3.0 \times 10^6$ [cells/cm$^2$], and it was found that the cells were immobilized at high density.

Further, when the fiber diameter was 100 micrometers, the cell density was equal to or lower than one-tenth of these with other fibers.

Example 2

Each nylon (trademark) mesh having a fiber diameter of 30 micrometers and an opening size of 5 to 200 micrometers was immersed in a culture medium [DMEM (Dulbecco's modified Eagle's medium)–high glucose (product of SIGMA, D6429), 10% FBS (fetal bovine serum)] containing mouse fibroblast 3T3L1 at $10^6$ cells/mL and subjected to shake culture. The culture medium was exchanged with a fresh culture medium every three days.

The cells adhering to each of the nylon (trademark) meshes proliferated without significant extension and were immobilized so as to bury the openings of each nylon mesh.

Figure 2:
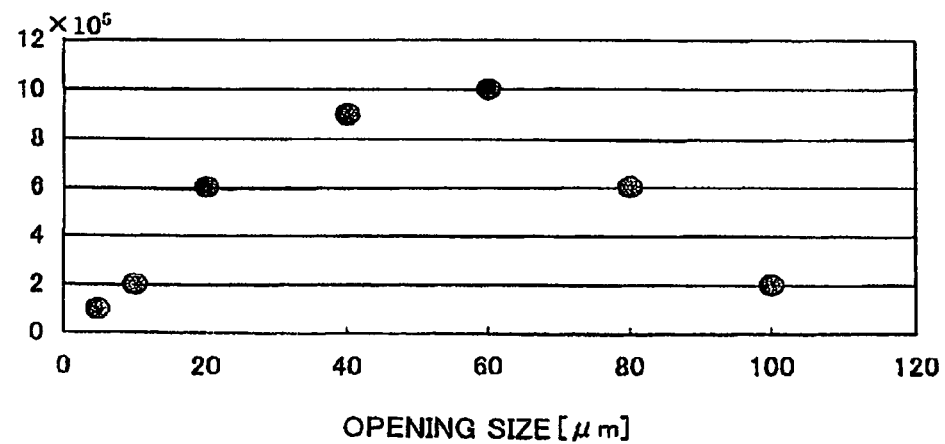
FIG. 2 is a graph that represents a relation between the cell density and opening size.

An area-based density of 3T3L1 immobilized to each mesh was measured after 30 days. The obtained results are shown in FIG. 2.

It was found that the cell density was high when the opening sizes of the meshes were 20 to 80 micrometers. When the opening sizes of the meshes were 20 to 80 micrometers, all of the openings were closed by the cells, and membrane-like biodevices to which animal cells were immobilized at high density were formed.

At this time, the density of the immobilized cells reached to $10^6$ [cells/cm$^2$], and it was ten times the cell density of $10^5$ when the cells adhered onto a plain surface confluently. Moreover, the maximum number of the cells piling up in the thickness direction was eight.

When the opening size of the mesh was equal to or smaller than 10 micrometers, the cell did not infiltrate into mesh and extended over the surface of the mesh. Since a distance between fibers was long in the mesh that had the opening size exceeding 80 micrometers, the cells could not bury the mesh, resulting in remaining of the openings.

Example 3

Figure 3:
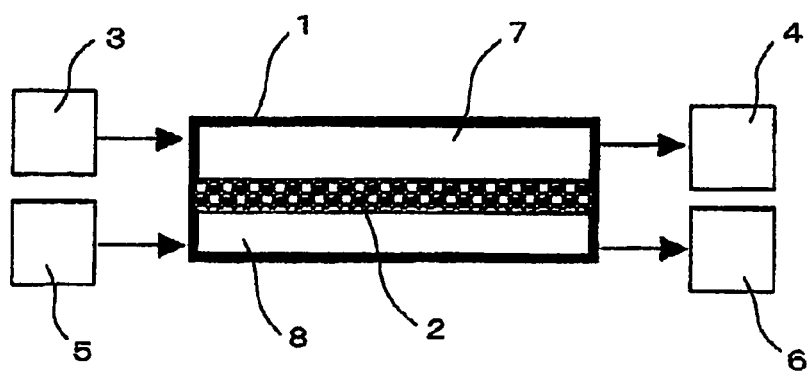
FIG. 3 is a cross sectional view that represents one example of a bioreactor of the present invention.

The same operations as those in example 2 were repeated to form a membrane-like biodevice in which cells were immobilized, and this membrane-like biodevice was set in a bioreactor container as shown in FIG. 3 to make a bioreactor, followed by carrying out cell culture.

FIG. 3 represents an example of the bioreactor of the present invention. A bioreactor container 1 is partitioned into two chambers of a first reaction chamber 7 and a second reaction chamber 8 by a membrane-like biodevice 2 in which cells have been immobilized.

In addition, a cell-maintenance culture medium (DMEM, 10% FBS) containing phenol red is stored in a first supply tank 3, and a cell-maintenance culture medium not containing phenol red is stored in a second supply tank 5.

The culture medium in the first supply tank 3 comes in contact with the membrane-like biodevice 2 in the first reaction chamber 7, and then discharged to a first recovery tank 4. On the other hand, the culture medium stored in the second supply tank 5 comes in contact with the device 2 in the second reaction chamber 8, and then discharged to a second recovery tank 6.

Oxygen and nutrients in the culture medium move from the first reaction chamber 7 to the device 2, move in the device 2 by diffusion, and are supplied to each cell. Metabolic products of the cells move from the device 2 to the second reaction chamber 8 and are collected in the second recovery tank 6.

Three days after operating this reactor, the measurement of phenol red contained in the culture medium in the second recovery tank 6 by absorbance resulted in a value lower than detection limitation. From this result, it was found that no convection passing through the inside of the device of the membrane-like biodevice 2 in which cells were immobilized took place and it could be confirmed that this membrane-like device 2 played a role of a partition.

According to the present invention, fibers that have a predetermined cross section, a sheet that has an opening, and the like are used as a carrier. Therefore, a linear biodevice, a membrane-like biodevice, and a bioreactor in which adhesive cells can be efficiently immobilized at high density and which are excellent in handling and applicability can be provided.

Further, in the membrane-like biodevice of the present invention, oxygen and nutrients essential for cells can be swiftly supplied.

Furthermore, in the preferred embodiment of the membrane-like biodevice of the present invention, it is also possible for adhesive cells to be immobilized in a membranous form at high density.

Still further, in the bioreactor of the present invention, two kinds of fluids are allowed to keep in contact with adhesive cells in a membranous form without being mixed with each other owing to a membrane-like biodevice in which the adhesive cells are immobilized in a membranous form, and therefore, it is possible to control and promote desired metabolic production efficiently.

Still further, in the bioreactor of the present invention, it is also possible to allow the adhesive cells in a membranous form to function as a selectively permeable membrane by selecting an appropriate cell. Accordingly, efficient continuous production and extraction of a useful metabolic product of deep-sea organisms by immobilizing cells of the deep-sea organisms become possible.

What is claimed is:

1. A membrane-like biodevice comprising;
a sheet having a plurality of openings of approximately the same square shape having a side length of from 20 to 80 micrometers and the openings are arranged at a predetermined pitch; and
approximately spherical adhesive cells adhering to the openings,
wherein a curved portion is present in a cross section on an inner edge of the openings.

2. The membrane-like biodevice according to claim 1, wherein a maximum length of the opening is from a particle diameter of the spherical adhesive cell immediately after cell division to ten times the particle diameter after cell growth.

3. The membrane-like biodevice according to claim 1, wherein the sheet is made of a mesh of fibers that have a curved portion in the cross section approximately perpendicular to the longitudinal direction.

4. The membrane-like biodevice according to claim 3, wherein the spherical adhesive cells grow densely so as to close the openings of the sheet.

5. The membrane-like biodevice according to claim 2, wherein the sheet is made of a mesh of fibers that have a curved portion in the cross section approximately perpendicular to the longitudinal direction.

6. The membrane-like biodevice according to claim 2, wherein the spherical adhesive cells grow densely so as to close the openings of the sheet.

* * * * *